United States Patent
Bybee

(10) Patent No.: US 6,679,881 B1
(45) Date of Patent: Jan. 20, 2004

(54) BIPOLAR TOOL FOR SURGICAL USE

(75) Inventor: David Byrum Bybee, 1208 Country Club Dr., Modesto, CA (US) 95356

(73) Assignee: David Byrum Bybee, Modesto, CA (US)

(*) Notice: Subject to any disclaimer, the term of this patent is extended or adjusted under 35 U.S.C. 154(b) by 0 days.

(21) Appl. No.: 09/680,831

(22) Filed: Oct. 6, 2000

(51) Int. Cl.7 ............................................... A61B 18/17
(52) U.S. Cl. .......................................... 606/51; 606/52
(58) Field of Search ............................... 606/43, 51, 52

(56) References Cited

U.S. PATENT DOCUMENTS

| | | | | |
|---|---|---|---|---|
| 2,888,927 A | * | 6/1959 | Fozard ......................... | 606/43 |
| 5,464,405 A | * | 11/1995 | Fujitsu et al. .................. | 606/51 |
| 5,603,712 A | * | 2/1997 | Koranda et al. ............... | 606/51 |
| 5,833,687 A | * | 11/1998 | Mehl et al. .................... | 606/43 |
| 6,048,341 A | * | 4/2000 | Hirakawa et al. .............. | 606/51 |
| 6,228,084 B1 | * | 5/2001 | Kirwan, Jr. .................... | 606/51 |
| 6,298,550 B1 | * | 10/2001 | Kirwan, Jr. .................... | 606/51 |

* cited by examiner

*Primary Examiner*—Lee Cohen
(74) *Attorney, Agent, or Firm*—Fredrikson & Byron, P.A.

(57) ABSTRACT

A bipolar tool for surgical use includes first and second electrically conductive arms each having a distal end and a proximal end wherein each of the first and second electrically conductive arms function as an independent electrode at the joining of the distal ends. A insulating element for electrically isolating the proximal ends of the first and the second electrically conductive arms from one another is provided. The proximal ends of the arms are embedded in the insulating element in such a manner that biases the distal ends of the arms normally in a joined or closed position. This feature enhances the dissecting capability of the bipolar tool. The surgical tool can also include an insulating covering extending from the proximal ends up to but not including the distal ends of the first and second electrically conductive arms for isolating the first and second electrically conductive arms from each other. The insulating element preferably includes prong members for connection to electrocoagulating equipment. The first and second electrically conductive arms may include a sharpened blade at a distal end or a planarly flattened or rounded distal end or a pointed tip at a distal end or a planarly flattened distal end. Preferably, the tool further comprises a tube extending from near the proximal end of at least one arm to an area near the distal end of the arm.

15 Claims, 1 Drawing Sheet

BIPOLAR TOOL FOR SURGICAL USE

FIELD OF THE INVENTION

This invention relates generally to a surgical tool and more specifically to a bipolar surgical tool for use in cutting tissue and coagulation of blood as well as placing and removing surgical materials into and from a surgical site.

RELEVANT ART

Bipolar cutting and coagulation tools are known in the art. These usually consist of dual armed instruments which are attached at their proximal end and progressively space apart as they reach the distal tip.

Such an instrument is described in U.S. Pat. No. 5,464, 405 issued to Kazuhiko Fujitsu et al., entitled "Bipolar Surgical Tweezers" which relates to an electric coagulating and incising tweezers with improved visual field of operation. The tweezers have a perfusion passage embedded in the surface on the inside of one of the arms.

Another instrument with similar characteristics is described in U.S. Pat. No. 5,603,712 issued to Frank C. Koranda et al., entitled "Bipolar Suction Tonsillar Dissector". The patent issued to Koranda et al. describes a bipolar suction tonsillar dissector having parallel arms which diverge as they near the distal, pointed end of the instrument. It includes a pair of arms connected by a connector plug to define forceps. One arm includes a tubular suction channel which may be connected to a vacuum source and presents an opening at the remote end through which undesired or excess fluids may be removed from the dissection site.

The principal difficulty with the foregoing instruments is that the tips are maintained in an open position while at rest. This creates difficulty in maneuvering into deep, small wounds due to the added risk of trauma to the wound site caused by the normally open, spaced apart ends. The problem is especially troublesome in the field of neurosurgery and more particularly in the area of brain surgery. It is often the case that a surgeon must enter into the brain through a very small wound opening. This is largely due to the need of perforating the cranium in the least invasive way. With the prior art instruments, a surgeon runs the risk of damaging nerves, as well as surrounding blood vessels, upon insertion of the instrument due to the normally biased open position of the instrument's arms.

A second difficulty with such prior art devices is that a surgeon normally has to change instruments when it becomes necessary to pick up objects such as gelfoam material, hemostatic agents, and the like. The prior art instruments are not convenient for that purpose due to the requirement of constant, applied manual pressure in order to maintain the tips of the arms closed. Furthermore, the tips, even when joined through closure of the arms, only make contact at the distal-most portion of the end of the arms, allowing for only minimal grasping capabilities. This has the effect of making the transport and positioning of surgical material difficult, often requiring changing instruments to better grasp objects and bring or remove them from the wound site.

Accordingly, there remains a need for improved bipolar tools having the capability of entering into small wounds without causing trauma, incise tissue, coagulate tissue and blood in order to prevent excessive blood loss and simultaneously, more effectively grasp materials that need to be inserted and removed from the wound site.

It is therefore an aspect of the present invention to provide an improved bipolar tool which provides for better grasping of surgical materials due to biasing the distal ends in a closed position. It is another aspect of the invention to provide an improved bipolar tool that is easily maneuverable in and out of deep, small wounds due to the distal ends being biased in a closed position. This reduces the chance of trauma to surrounding nerves and blood vessels.

A further aspect of the invention is to facilitate viewing of the surgical site during use of the inventive forceps due to a bayonet bend of the longitudinal arms, thereby angling away from the surgeon's view. It is still another aspect of the present invention to accomplish the above-stated objects by utilizing a tool which is simple in design and use and efficient to manufacture.

The foregoing advantages of the invention are illustrative of those that can be achieved by the present invention and are not intended to be exhaustive or limiting of the possible advantages which can be realized. Thus, these and other aspects and advantages of the invention will be apparent from the description herein or can be learned from practicing the invention, both as embodied herein or as modified in view of any variation which may be apparent to those skilled in the art. Accordingly, the present invention resides in the novel apparatus, arrangements, combination and improvements herein shown and described.

SUMMARY OF THE INVENTION

The present invention generally relates to a bipolar tool for cutting, manipulating, dissecting and cauterizing tissue and grasping objects which includes first and second arms that are electrically conductive and electrically isolated from one another. Each arm carries opposite electrical charges through the metal of the arm itself or through a conducting wire that runs from the distal ends of the arms to an electrical connector at the proximal end. These arms have distal and proximal ends wherein the arms function as independent electrodes. The distal ends of the arms of the bipolar tool are biased in a closed position, which forces the distal ends of the arms together to enable the dissection of tissue. In its resting state with no force applied to the bipolar tool, the distal ends are forced together in a closed position by the spring-like tension due to the construction of the bipolar tool and the composition of the material from which the arms are made as well as the shape of the arms. The tool has an insulating member 16 which is attached to the arms at their proximal ends. The insulating member 16 can be made of any insulating material that is non-conductive to electricity. The arms are at opposite sides of a crossover point and extend from the proximal end towards the distal end in a substantially parallel relationship until reaching the crossover point. The arms curve towards and crossover each other to opposite sides of the crossover point and realign in a substantially parallel relationship as they extend towards the distal end of the tool.

Thus, there is disclosed, a bipolar tool for surgical use comprising first and second electrically conductive arms each having a distal end and a proximal end. Each of the first and second electrically conductive arms function as an independent electrode at the joining of the distal ends. The bipolar tools also includes an insulating element is used for electrically isolating the proximal ends of the first and second electrically conductive arms from one another; said insulating element and said arms are configured for biasing the distal ends of the first and second electrically conductive arms in a normally joined or closed position.

The bipolar tool according to the invention may also additionally comprise an insulating covering extending from the proximal ends up to, but not including, the distal ends of the first and second electrically conductive arms for isolating the first and second electrically conductive arms from each other. The tool preferably has a tapered tip at the distal end of at least one of the arms and at least one of the arms has a planarly flattened distal end. The tool preferably comprises an irrigation tube extending from near said proximal end of at least one arm to an area near the distal end of said arm.

In another embodiment, the tool includes pointed tips at the distal ends of the first and second electrically conductive arms. In yet another embodiment, the arms are generally planarly flattened from the distal end to the proximal end of the arm.

There is also disclosed a bipolar tool for surgical use comprising a first electrically conductive arm which has a distal end and a proximal end. The first electrically conductive arm functions as an independent electrode and a second electrically conductive arm has a distal end and a proximal end. The second electrically conductive arm functions as an independent electrode and runs parallel on one side of the first electrically conductive arm at the proximal end to converge at the distal end from the other side after a crossover point. An insulating element for electrically isolating said proximal ends of said first electrically conductive arm and said second electrically conductive arm from one another, wherein said insulating element and said arms are configured to bias the distal ends of the first and second electrically conductive arms in a normally joined position.

In a further embodiment, the tool includes an insulating covering extending from the proximal ends up to, but not including, the distal ends of the first and second electrically conductive arms for isolating the first electrically conductive arm from the second electrically conductive arm.

DETAILED DESCRIPTION OF THE PREFERRED EMBODIMENT

Figure 4:
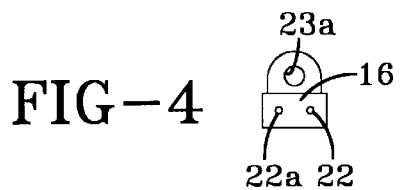
FIG. 4 is a top plan view of the insulator of the bipolar tool.

Referring now to the drawings, in which like numerals refer to like components, there is disclosed a preferred embodiment of the present invention. A bipolar tool is described which, while being extremely maneuverable during an operation, permits careful and accurate placement of medical items without the risk of unnecessary trauma to the patient. This bipolar tool also enhances the dissection of tissue and cauterization.

Figure 1:
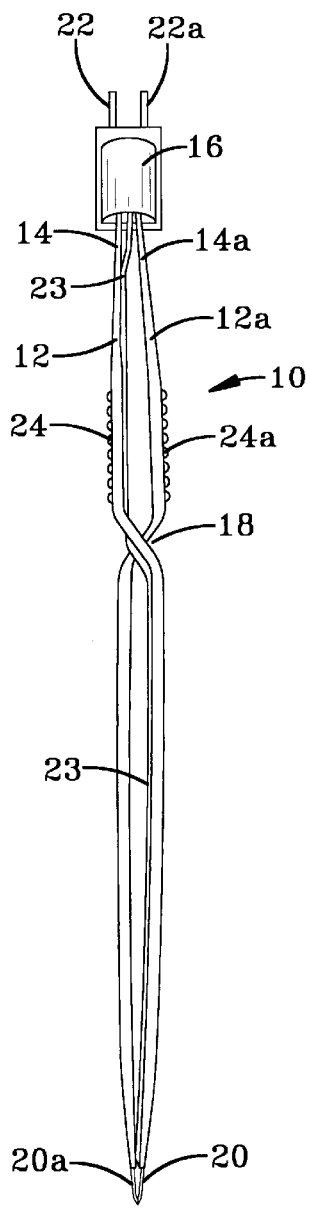
FIG. 1 is a plan view of a bipolar tool according to the invention in the resting, closed position.

FIG. 1 discloses a general arrangement of a bipolar tool 10 having two arms 12 and 12a (which can be flat or round) which are connected at their proximal ends 14 and 14a to an insulator 16. The distal ends 20 and 20a of the arms provide relative poles for the passage of electrical current therethrough when joined, or more appropriately, when tissue is clasped therebetween for bipolar coagulation. The arms crossover each other at point 18, and meet at distal ends 20 and 20a, respectively. The insulator 16 is constructed of a non-conducting material, such as a natural or synthetic polymer, or a conducting material that has been insulated to prevent electrical conductivity between arms 12 and 12a while allowing for attachment of arms 12 and 12a and preventing them from coming into direct contact with each other except at the distal ends 20 and 20a when the tool is in the resting or closed state. Arms 12 and 12a are substantially encased, at their proximal ends, within the insulator 16 in such a manner that the arms are configured for biasing the distal ends of the arms in a normally joined or closed position. In this way, arms 12 and 12a are positioned at proximal ends 14 and 14a within the insulator 16 so as to extend distally from insulator 16 in a substantially parallel relationship but initially diverging slightly outward from the tool's proximal to distal axis. Preferably, the device according to the invention is electrically insulated except for the distal ends 20 and 20a by an insulating coating, preferably of friction-resistant synthetic resin material such as polytetrafluoroethylene (also known as PTFE or by the trademark Teflon®). Each arm 12 and 12a is preferably made of an electrically conductive material of suitable corrosion-resistance and hardness, such as stainless steel or titanium. In the event a non-conductive material is used to prepare the arms, accommodations must be made for a wire to connect the distal ends of the arms 20 and 20a with the prongs 22 and 22a. In any event, the material from which the arms are constructed must permit a sufficient degree of resiliency to be used in a forceps-like manner.

The arms 12 and 12a are positioned at opposite sides of a crossover point 18 and extend from the proximal end towards the distal end in a substantially parallel relationship until reaching a medial portion of the tool 10 located between the proximal and distal ends. Upon reaching the medial point, each arm 12 and 12a curves into and crosses over to the opposite side at the crossover point 18 and is subsequently realigned to once again assume a substantially parallel relationship with the other arm as it extends towards the distal portion of the instrument. In its resting state with no force applied to the bipolar tool 10, the distal ends 20 and 20a are forced together in a closed position by a spring-like tension due to the construction of tool 10 and the composition of the material from which the arms are made as well as the shape of the arms and the configuration of the arms embedded in the insulator 16. The tool 10 preferably also has an irrigation tube 23 used to carry fluid toward the distal end 20. The irrigation tube 23 extends from the port 23a (see FIG. 4) in insulator 16 at the top of tool 10 along arm 12 past the cross-over point 18 and down near distal end 20. The irrigation tube 23 is preferably attached to arm 12 from near the top of tool 10 down to near the distal end 20, but the irrigation tube 23 does not have to be welded or physically attached to arm 12 as long as the irrigation tube 23 extends from port 23a to an area near the distal end 20. The irrigation tube 23 can be used to provide sterile saline solution or other fluid to the area of distal end 20 or it can be used to suction fluid and material from the area around distal end 20. The irrigation tube 23 can be connected to a hose or other source of saline solution or suction through port 23a.

Figure 2:
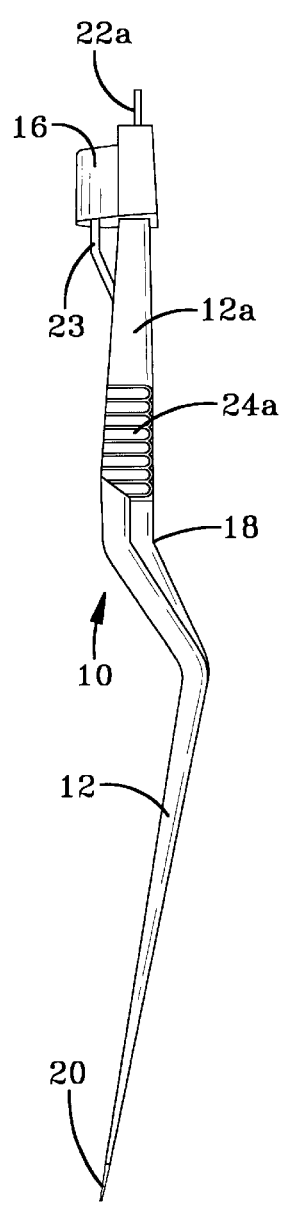
FIG. 2 is a plan view of the bipolar tool of FIG. 1 illustrating a side view of the tool in the resting, closed position.

Two prongs 22 and 22a are embedded in and extend outwardly from insulator 16 to allow for connection to electrocoagulating equipment commonly known to those skilled in the art. Prong 22 is electrically connected to arm 12 and prong 22a is connected to arm 12a. Prongs 22 and 22a are made of a conductive metal and constructed in a conventional way. The prongs 22 and 22a are conventionally spaced for attachment to electrocoagulating equipment. Distal ends 20 and 20a may be in the form of tapered and/or pointed tips, planarly flattened ends, a sharpened blade or the like, as well as any combination thereof Referring now to FIG. 2, arms 12 and 12a, as viewed from the side, are bayoneted at a point 18 between proximal ends 14 and 14a and distal ends 20 and 20a of the tool 10. Tool 10 also include grooves 24 and 24a on the proximal ends of the arms 12 and 12a allowing for gripping and the application of pressure. The bayoneted configuration permits a clear view of distal ends 20 and 20a for placement of items and operation of tool 10 for cutting and coagulation.

Figure 3:
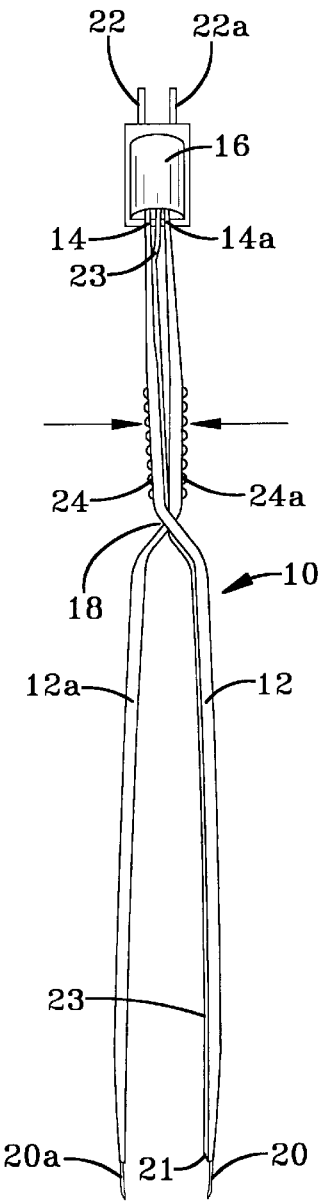
FIG. 3 shows a plan view of the bipolar tool of FIG. 1 illustrating the bipolar tool in the open position.

FIG. 3 illustrates tool 10 with distal ends 20 and 20a in an open position after arms 12 and 12a are pressed in towards each other at grooves 24 and 24a thereby forcing distal ends 20 and 20a, which are normally biased into a closed position, to separate into an open position.

FIG. 4 is a top view of the insulating element 16. Port 23a is configured to allow for attachment of vacuum or liquid sources. In similar fashion, prongs 22 and 22a are configured to provide convenient attachment to electrocoagulating equipment.

In operation, tool 10 is held at grooves 24 and 24a by a surgeon. It is then inserted into a wound in the normally biased closed position. Once inside the wound, application of pressure to arms 12 and 12a at grooves 24 and 24a open distal ends 20 and 20a of tool 10 and cause them to spring open, allowing for incision, manipulation, dissection or coagulation of tissue and blood. If external material needs to be inserted into a wound, the surgeon opens distal ends 20 and 20a of arms 12 and 12a, respectively, by applying pressure at grooves 24 and 24a, grasps the required material and releases pressure on grooves 24 and 24a. Releasing pressure at grooves 24 and 24a causes distal ends 20 and 20a of arms 12 and 12a to return to their normal position, closed. Upon insertion of bipolar tool 10 into the wound, the surgeon need not apply any pressure to the arms while placing the material, due to the normally biased closed position of the arms 12 and 12a. Upon placement of the material, the surgeon applies pressure to grooves 24 and 24a to release the material held between distal ends 20 and 20a. This allows greater control for the surgeon in manipulation and dissection of tissue and placement of the material.

Industrial Applicability

The medical community is constantly in search of improved tools to fiacilitate surgical procedures. While bipolar surgical tweezers and bipolar suction tonsillar dissectors have been known for some time, there are still problems associated with these prior art devices. The present invention advances the state of the art in surgical tools by providing a bipolar tool that uses a bayonet configuration and a biasing member to keep the electrically conductive arms in a normally joined position. Although the present invention has been described in detail with particular reference to preferred embodiments, it should be understood that the invention is capable of other and different embodiments and its details are capable of modifications in various respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed:

1. A bipolar tool for surgical use comprising:
    a) first and second electrically conductive arms each having a distal end and a proximal end wherein each of said first and second electrically conductive arms function as an independent electrode at the joining of said distal ends, said first and second electrically conductive arms being configured to crossover one another at a point located approximately medial between the proximal ends and the distal ends thereof;
    b) insulating element for electrically isolating said proximal ends of said first and said second electrically conductive arms from one another; and
    c) said insulating element and said arms are configured for biasing said distal ends of said first and second electrically conductive arms in a normally joined position.

2. A bipolar tool for surgical use according to claim 1 additionally comprising an insulating covering extending from said proximal ends up to but not including said distal ends of said first and second electrically conductive arms for isolating said first and second electrically conductive arms from each other.

3. A bipolar tool for surgical use according to claim 1 wherein said insulating element comprises prong members for connection to electrocoagulating equipment.

4. A bipolar tool for surgical use according to claim 1 wherein said first and second electrically conductive arms include a sharpened blade at a distal end.

5. A bipolar tool for surgical use according to claim 1 wherein said first and second arms are planarly flattened from the distal end to the proximal end of the arm.

6. A bipolar tool for surgical use according to claim 1 wherein said first and second arms include a pointed tip at the distal end.

7. A bipolar tool for surgical use according to claim 1 wherein at least one of said first and second arms includes a planarly flattened distal end.

8. A bipolar tool for surgical use comprising:
    a) first electrically conductive arm having a distal end and a proximal end, said first electrically conductive arm to function as an independent bipolar electrode;
    b) second electrically conductive arm having a distal end and a proximal end, said second electrically conductive arm to function as an independent bipolar electrode, said second electrically conductive arm to run parallel on one side of said first electrically conductive arm at said proximal end and to converge at said distal end from an other side after a crossover point, said crossover point being located approximately medially between the proximal and distal ends;
    c) insulating element for electrically isolating said proximal ends of said first electrically conductive arm and said second electrically conductive arm from one another, wherein said insulating elements and said arms are configured for biasing said distal ends of said first and second arms in a normally joined position.

9. A bipolar tool for surgical use according to claim 8 also including insulating covering extending from said proximal ends up to but not including said distal ends of said first electrically conductive arm and second electrically conductive arm for isolating said first electrically conductive arm and said second electrically conductive arm from each other.

10. A bipolar tool for surgical use according to claim 8 wherein said insulating element includes prong members for connection to electrocoagulating equipment.

11. A bipolar tool for surgical use according to claim 8 wherein said first electrically conductive arm includes a sharpened blade at a distal end.

12. A bipolar tool for surgical use according to claim 8 wherein said first electrically conductive arm includes a planarly flattened distal end.

13. A bipolar tool for surgical use according to claim 8 wherein said first electrically conductive arm includes a pointed tip at a distal end.

14. A bipolar tool for surgical use according to claim 8 wherein at least one arm is planarly flattened.

15. A bipolar tool for surgical use according to claim 8 wherein at least one arm is rounded.

* * * * *